United States Patent
Pacetti et al.

(10) Patent No.: US 9,610,385 B2
(45) Date of Patent: Apr. 4, 2017

(54) METHOD OF FABRICATING AN IMPLANTABLE MEDICAL DEVICE COMPRISING A RAPAMYCIN DERIVATIVE

(71) Applicant: Abbott Cardiovascular Systems Inc., Santa Clara, CA (US)

(72) Inventors: Stephen D. Pacetti, San Jose, CA (US); Julia Fox, San Carlos, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 793 days.

(21) Appl. No.: 13/789,473

(22) Filed: Mar. 7, 2013

(65) Prior Publication Data
US 2014/0250836 A1    Sep. 11, 2014

(51) Int. Cl.
*A61F 13/00* (2006.01)
*A61K 31/44* (2006.01)
*B65B 55/18* (2006.01)
*B23P 25/00* (2006.01)
*A61L 31/08* (2006.01)
*A61L 31/16* (2006.01)
*B65B 55/12* (2006.01)
*A61L 31/14* (2006.01)

(52) U.S. Cl.
CPC ............. *A61L 31/08* (2013.01); *A61L 31/143* (2013.01); *A61L 31/16* (2013.01); *B65B 55/12* (2013.01); *A61L 2300/416* (2013.01); *A61L 2420/02* (2013.01); *Y10T 29/49885* (2015.01)

(58) Field of Classification Search
None
See application file for complete search history.

(56) References Cited

U.S. PATENT DOCUMENTS

| | | |
|---|---|---|
| 6,004,973 A | 12/1999 | Guitard et al. |
| 6,605,613 B2 | 8/2003 | Navarro et al. |
| 6,852,729 B2 | 2/2005 | Navarro et al. |
| 7,297,703 B2 | 11/2007 | Navarro et al. |
| 7,572,804 B2 | 8/2009 | Navarro et al. |
| 7,741,338 B2 | 6/2010 | Navarro et al. |
| 8,003,122 B2 | 8/2011 | Zhao |
| 8,685,433 B2 | 4/2014 | Kleiner et al. |
| 2006/0240070 A1 | 10/2006 | Cromack et al. |
| 2007/0084144 A1* | 4/2007 | Labrecque ............ A61B 19/026 53/425 |
| 2009/0269479 A1* | 10/2009 | Pacetti .................... A61L 31/10 427/2.24 |

FOREIGN PATENT DOCUMENTS

| | | | |
|---|---|---|---|
| EP | 1 586 338 | 10/2005 | |
| GB | WO 97/03654 | * 2/1997 | ............ A61K 9/14 |
| WO | WO 97/03654 | 2/1997 | |
| WO | WO 2012/017449 | 2/2012 | |
| WO | WO 2012/162007 | 11/2012 | |

OTHER PUBLICATIONS

International Search Report for PCT/US2014/021153, mailed Jul. 7, 2014, 9 pgs.

* cited by examiner

*Primary Examiner* — Jeffrey T Palenik
(74) *Attorney, Agent, or Firm* — Squire Patton Boggs (US) LLP (57) ABSTRACT

This invention relates to an method of manufacture of an implantable medical device comprising an oxygen-sensitive rapamycin derivative that is protected by addition of an antioxidant during the manufacturing process where the amount of antioxidant added at the outset of the processing is such that when the device is fully fabricated, sterilized and packaged the amount of antioxidant has reduced to a minimal, preferably non-detect, amount.

24 Claims, 2 Drawing Sheets

METHOD OF FABRICATING AN IMPLANTABLE MEDICAL DEVICE COMPRISING A RAPAMYCIN DERIVATIVE

FIELD

This invention relates to a method of fabricating an implantable medical device that includes a drug reservoir layer comprising a rapamycin derivative drug wherein the steps in the process minimize exposure of the drug to harsh processing conditions, eliminate the need to isolate the drug as a dry solid, and ameliorate deterioration of the drug caused by the general oxygen-sensitivity of this class of drugs due to the presence of a conjugated triene in their macrocyclic ring structure.

BACKGROUND

Until the mid-1980s, the accepted treatment for coronary atherosclerosis, i.e., narrowing of the coronary artery(ies) was coronary by-pass surgery. While being quite effective and having evolved to a relatively high degree of safety for an invasive procedure, by-pass surgery still involves potentially serious complications and generally results in an extended recovery period.

With the advent of percutaneous transluminal coronary angioplasty (PTCA) in 1977, the scene changed dramatically. Using catheter techniques originally developed for heart exploration, inflatable balloons were deployed to re-open occluded regions in arteries. The procedure was relatively non-invasive, took a short time compared to by-pass surgery and recovery time was minimal. However, PTCA brought with it its own problems including vasospasm, elastic recoil of the stretched arterial wall and restenosis, the re-clogging of the treated artery due to neointimal hyperplasia in the vicinity of the procedure, any of which could undo much of what had been accomplished.

The next improvement, advanced in the mid-1980s, was the use of a stent to maintain a luminal diameter that had been re-established using PTCA. This for all intents and purposes put an end to vasospasm and elastic recoil but did not resolve the issue of restenosis. That is, prior to the introduction of stents, restenosis occurred in about 30 to 50% of patients undergoing PTCA. Stenting reduced this to about 15 to 30%, a substantial improvement but still more than desirable.

In 2003, the drug-eluting stent (DES) was introduced. The drugs initially used with DESs were cytostatic compounds, that is, compounds that curtailed the proliferation of cells that fostered restenosis. With DESs, the occurrence of restenosis was reduced to about 5 to 7%, a relatively acceptable figure. However, the use of DESs engendered yet another complication, late stent thrombosis, the forming of blood clots at some time after the stent was in place. It was hypothesized that the formation of blood clots was most likely due to delayed healing, a side-effect of the use of cytostatic drugs. Thus, other types of drugs were sought to reduce the incidence of late stent thrombosis as well as other complications related to the use of cytostatic agents. A promising solution was found in the anti-proliferative family of compounds, in particular rapamycin and its derivatives, which appeared surprisingly effective. DESs comprising members of the rapamycin family of compounds were extensively studied and several have become commercial products. It was found, however, that, due at least in part to the fact that there are three conjugated double bonds in rapamycin and its pharmaceutically active derivatives, the entire family of rapamycin derivative drugs is sensitive to oxidative and free radical induced degradation. That is, oxygen in and around a DES containing the macrocyclic triene fosters the formation of radical species that in turn initiate auto-oxidation of the triene moiety. The response to this negative property of the compounds was obvious to those skilled in the art: protect the rapamycin derivatives by including a pharmaceutically acceptable antioxidant with the drug both as an isolated solid as synthesized and purified and in a drug reservoir layer containing the rapamycin derivative on a DES.

The problem is that many antioxidants including those suitable for use on DESs are not particularly salutary to patients. This, together with the fact that, once fabricated and packaged in an essentially oxygen-free atmosphere protected from light, rapamycin derivative drugs are actually reasonably stable suggests that, in addition to in general reducing the exposure of the drug to harsh processing conditions, it would be beneficial to have an antioxidant present during the fabrication of a rapamycin derivative-containing DES but have a little as possible remaining once the DES is mounted on a carrier vehicle, sterilized and packaged in a light-tight, inert atmosphere container or once the DS has been implanted in a patient. The present invention provides a method of accomplishing this goal.

SUMMARY

Thus, in one aspect this invention relates to a method of fabricating an implantable medical device comprising a rapamycin derivative drug, the method comprising:
synthesizing a rapamycin derivative drug;
purifying the rapamycin derivative drug using a technique that results in substantially pure rapamycin derivative drug dissolved in a solvent, wherein:
   the solvent used in the purification technique is suitable for preparation of a coating composition comprising the rapamycin derivative drug;
determining the percent by weight of the rapamycin derivative in the solvent;
adjusting the amount of solvent such that the weight percent rapamycin derivative drug in the solvent is that desired in a coating composition to be applied to an implantable medical device;
adding a desired weight percent, based on the weight of rapamycin derivative drug, of an pharmaceutically acceptable antioxidant stabilizer to form the coating composition; and
disposing the coating composition on the implantable medical device to form a drug reservoir layer.

In an aspect of this invention, the method herein further comprisesaddition of a matrix polymer to the coating composition before disposing the composition on an implantable medical device.

In an aspect of this invention, the method herein further comprises drying the drug reservoir layer.

In an aspect of this invention, the method herein further comprises mounting the implantable medical device on a carrier vehicle.

In an aspect of this invention, the carrier vehicle is a catheter.

In an aspect of this invention, the carrier vehicle with mounted implantable device is sterilized.

In an aspect of this invention, sterilization comprises ethylene oxide sterilization, e-beam sterilization or gamma sterilization.

In an aspect of this invention, the sterilized delivery device/implantable device is packaged in a light-tight container under an inert atmosphere.

In an aspect of this invention, the synthesized rapamycin drug is selected from the group consisting of a 40-O-substituted rapamycin, everolimus, temsirolimus, deforolimus, ridaforolimus, merilimus, biolimus, umirolimus and 16-pent-2-ynyloxy-32(S)-dihydrorapamycin.

In an aspect of this invention, the synthesized rapamycin drug is selected from the group consisting of zotarolimus, ABT-578, a 16-O-substituted rapamycin, novolimus, or myolimus.

In an aspect of this invention, the antioxidant stabilizer is selected from the group consisting of a butylated phenol, butylated hydroxytoluene (BHT), butylated hydroxyanisole, t-butylhydroquinone, quinone, an alkyl gallate, methyl gallate, ethyl gallate, propyl gallate, octyl gallate, docecyl gallate, resveratrol, cysteine, n-acetylcysteine, bucillamine, glutathione, 7-hydroxyethylrutoside, carvedilol, vitamin C, ascorbyl palmitate, fumaric acid, a tocopherol, α-tocopherol, α-tocopherol acetate, a tocotrienol, vitamin E, lycopene, a flavonoid, a carotenoid, carotene and combinations thereof.

In an aspect of this invention, the antioxidant stabilizer is BHT.

In an aspect of this invention, purifying the synthesized rapamycin derivative drug is selected from the group consisting of elution (column) chromatography, high performance liquid chromatography, high performance countercurrent chromatography, planar chromatography, supercritical fluid chromatography, liquid-liquid extraction and liquid-solid extraction.

In an aspect of this invention, the solvent involved in the purification process that is also suitable as a the solvent for a coating composition is selected from the group consisting of methanol, ethanol, propanol, n-propanol, isopropanol, butanol, pentane, hexane, heptane, octane, nonane, methyl acetate, ethyl acetate, propyl acetate, butyl acetate, toluene, xylene, acetone, methyl ethyl ketone (MEK), cyclopentanone, cyclohexanone, diethyl ether, dipropyl ether, diisopropyl ether, tetrahydrofuran, dioxane, dimethyl formamide, dimethylacetamide, dimethyl sulfoxide and combinations thereof.

In an aspect of this invention, adjusting the amount of solvent to a give a selected weight/weight percent rapamycin derivative drug in solvent comprises removing solvent or adding solvent to the coating composition.

In an aspect of this invention, the polymer is selected from the group consisting of a polyester, poly(L-lactide), poly(D-lactide), poly(D,L-lactide), poly(meso-lactide), poly(L-lactide-co-glycolide), poly(D-lactide-co-glycolide), poly(D,L-lactide-co-glycolide), poly(meso-lactide-co-glycolide), poly(caprolactone), poly(L-lactide-co-caprolactone), poly(glycolide-co-caprolactone), poly(hydroxyvalerate), poly(hydroxybutyrate), poly(ethylene glycol-co-butylene terephthalate), poly(n-butyl methacrylate), a fluoropolymer, poly(vinylidene fluoride-co-hexafluoropropylene) and blends and copolymer thereof.

In an aspect of this invention, the polymer is poly(vinylidene fluoride-co-hexafluoropropylene).

In an aspect of this invention, disposing the coating composition on the implantable medical device to form a drug reservoir layer comprises spray coating.

In an aspect of this invention, the implantable medical device is a stent.

In an aspect of this invention, the rapamycin derivative drug is everolimus.

In an aspect of this invention, the weight percent BHT based on the weight of everolimus present on the stent is 0.001 to 0.01%.

In an aspect of this invention, the amount of BHT remaining on the stent after all of the process steps are completed is non-detectable.

DETAILED DESCRIPTION

DISCUSSION

Use of the singular herein includes the plural and vice versa unless expressly otherwise stated. That is, "a" and "the" refer to one or more of whatever the word modifies. For example, "a pharmaceutically acceptable antioxidant" includes one such oxidant, two such oxidants or, under the right circumstances, an even greater number of antioxidants. By the same token, words such as, without limitation, "coatings" and "layers" refer to one coating or layer as well as to a plurality of coatings or layers unless, again, it is expressly stated or obvious from the context that such is not intended.

As used herein, words of approximation such as, without limitation, "about" "substantially," "essentially" and "approximately" mean that the feature so modified need not be exactly that which is expressly described but may vary from that written description to some extent. The extent to which the description may vary will depend on how great a change can be instituted and have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by ±15%.

As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device is physically removed; or until the device biodegrades usually as the result of the intentional use of a biodegradable substance for the fabrication of the device such that the device degrades over a predetermined timespan. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses, vascular grafts, self-expandable stents, balloon-expandable stents, stent-grafts, grafts, artificial heart valves and cerebrospinal fluid shunts.

While implantable medical devices can serve several concurrent purposes and such are within the scope of this invention, an implantable medical device specifically designed and intended solely for the localized delivery of a therapeutic agent is within the scope of this invention.

Described by this invention, however, are drug-device combination products which have primarily a device function with an added therapeutic agent to mitigate a known complication of the device, namely the occurrence of restenosis subsequent to implantation of a stent, a presently preferred implantable medical device of this invention, in a vessel for the purpose of maintain the patency of the vessel after such has been mechanically re-established by, for example, PTCA.

A stent refers generally to a device used to hold tissue in place in a patient's body. Particularly useful stents, however, are those used for the maintenance of the patency of a vessel in a patient's body when the vessel is narrowed or closed due to diseases or disorders including, without limitation, tumors (in, for example, bile ducts, the esophagus, the trachea/bronchi, etc.), benign pancreatic disease, coronary artery disease, carotid artery disease and peripheral arterial disease such as atherosclerosis, restenosis and vulnerable plaque. Vulnerable plaque (VP) refers to a fatty build-up in an arterial wall thought to be caused by inflammation and atherosclerosis. The VP is covered by a thin fibrous cap that can rupture leading to blood clot formation. A stent can be used to strengthen the wall of the vessel in the vicinity of the VP and act as a shield against such rupture. A stent can be used, without limitation, in the neurological, carotid, coronary, pulmonary, renal, iliac, femoral, popliteal, and tibial arteries as well as in biliary applications and other peripheral vasculatures. A stent can be used in the treatment or prevention of disorders such as, without limitation, thrombosis, restenosis, hemorrhage, vascular dissection or perforation, vascular aneurysm, chronic total occlusion, claudication, anastomotic proliferation, bile duct obstruction and ureter obstruction.

In addition to the above uses, stents may also be employed for the localized delivery of therapeutic agents to specific treatment sites in a patient's body. In fact, therapeutic agent delivery may be the sole purpose of the stent or the stent may be primarily intended for another use such as those discussed above with drug delivery providing an ancillary benefit. A DES is a non-limiting example of an implantable medical device of this invention. The primary purpose of a DES is to maintain the patency of a vascular lumen, while the drug on the stent serves to mitigate medical conditions ancillary to the implantation of the stent.

A stent used for patency maintenance is usually delivered to the target site in a compressed state and then expanded to fit the vessel into which it has been inserted. Once at a target location, a stent may be self-expandable or balloon expandable. In any event, due to the expansion of the stent, any coating thereon must be flexible and capable of elongation.

As used herein, "device body" refers to a fully formed implantable medical with an outer surface to which no coating or layer of material different from that of which the device itself is manufactured has been applied. A common example of a device body is a bare metal stent (BMS), which, as the name implies, is a fully-formed, usable stent that has not been coated with a layer of any material different from the metal of which it is made on any surface that is in contact with bodily tissue or fluids. Of course, device body refers not only to BMSs but to any uncoated device regardless of what it is made. Device bodies comprised of bioresorbable polymers and corrodible metals are also known.

Implantable medical devices made of virtually any material, i.e., materials presently known to be useful for the manufacture of implantable medical devices and materials that may be found to be so in the future, may be used in the method of this invention. For example, without limitation, an implantable medical device useful with this invention may be made of one or more biocompatible metals or alloys thereof including, but not limited to, cobalt-chromium alloy (ELGILOY, L-605), cobalt-nickel alloy (MP-35N), 316L stainless steel, high nitrogen stainless steel, e.g., BIODUR 108, nickel-titanium alloy (NITINOL), tantalum, platinum, platinum-iridium alloy, iron-platinum-chromium alloy, gold and combinations thereof.

Implantable medical devices may also be made of polymers that are biocompatible and biostable or biodegradable, the latter term including bioabsorbable, bioresorbable and bioerodable.

As used herein, a "biocompatible" polymer refers to a polymer wherein both its chemically intact, as synthesized, form and its degradation products are not, or at least are minimally toxic to living tissue; do not, or at least minimally and reparably injure living tissue; and do not, or at least minimally and controllably causes an immunological reaction in living tissue. Biocompatible polymers of this invention may be biostable or biodegradable where "biodegradable" simply means that the polymer will be decomposed over time when exposed to a physiological environs, i.e. to the conditions present in a patient's body such as pH, the presence of enzymes, body temperature, etc. "Biostable," on the other hand, refers to a polymer that does not significantly break down under physiological conditions for essentially the entire duration of its residency in a patient's body.

Examples of biocompatible, relatively biostable polymers that may be used with an implantable medical device of this invention include, without limitation, polyacrylates, polymethacryates, polyureas, polyurethanes, polyolefins, polyvinylhalides, polyvinylidenehalides, polyvinylethers, polyvinylaromatics, polyvinylesters, polyacrylonitriles, polysiloxanes, alkyd resins and epoxy resins.

Biocompatible, biodegradable polymers include naturally-occurring polymers such as, without limitation, collagen, gelatin, chitosan, alginate, fibrin, fibrinogen, cellulosics, starches, dextran, dextrin, hyaluronic acid, heparin, glycosaminoglycans, polysaccharides and elastin.

One or more synthetic or semi-synthetic biocompatible, biodegradable polymers may also be used to fabricate an implantable medical device body of this invention. As used herein, a synthetic polymer refers to one that is created wholly in the laboratory while a semi-synthetic polymer refers to a naturally-occurring polymer that has been chemically modified in the laboratory. Examples of synthetic biodegradable polymers include, without limitation, polyphosphazines, polyphosphoesters, polyphosphoester urethane, polyhydroxyacids, polyhydroxyalkanoates, polyanhydrides, polyesters, polyorthoesters, polyamino acids, polyoxymethylenes, poly(ester-amides) and polyimides.

Other biocompatible polymers that may be used to fabricate the device to be coated with a macrocyclic triene lactone drug/antioxidant stabilizer drug reservoir layer of this invention include, without limitations, polyesters, polyhydroxyalkanoates (PHAs), poly(ester amides) that may optionally contain alkyl, amino acid, PEG and/or alcohol groups, polycaprolactone, poly(L-lactide), poly(D,L-lactide), poly(D,L-lactide-co-PEG) block copolymers, poly(D,L-lactide-co-trimethylene carbonate), polyglycolide, poly(lactide-co-glycolide), polydioxanone (PDS), polyorthoester, polyanhydride, poly(glycolic acid-co-trimethylene carbonate), polyphosphoester, polyphosphoester urethane, poly(amino acids), polycyanoacrylates, poly(trimethylene carbonate), poly(iminocarbonate), polycarbonates, polyurethanes, copoly(ether-esters) (e.g. PEO/PLA), polyalkylene oxalates, polyphosphazenes, PHA-PEG, and combinations thereof. The PHA may include poly(α-hydroxyacids), poly(β-hydroxyacid) such as poly(3-hydroxybutyrate) (PHB), poly(3-hydroxybutyrate-co-valerate) (PHBV), poly(3-hydroxyproprionate) (PHP), poly (3-hydroxyhexanoate) (PHH), or poly(4-hydroxyacid) such as poly poly(4-hydroxybutyrate), poly(4-hydroxyvalerate), poly(4-hydroxyhexanoate), poly(hydroxyvalerate), poly(tyrosine carbonates), poly(tyrosine arylates), poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly (4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly (L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(anhydrides), poly (tyrosine carbonates) and derivatives thereof, poly(tyrosine ester) and derivatives thereof, poly(imino carbonates), poly (glycolic acid-co-trimethylene carbonate), polyphosphoester, polyphosphoester urethane, poly(amino acids), polycyanoacrylates, poly(trimethylene carbonate), poly (iminocarbonate), polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. poly(ethylene oxide-co-lactic acid) (PEO/PLA)), polyalkylene oxides such as poly(ethylene oxide), poly(propylene oxide), poly(ether ester), polyalkylene oxalates, phosphoryl choline containing polymer, choline, poly(aspirin), polymers and co-polymers of hydroxyl bearing monomers such as 2-hydroxyethyl methacrylate (HEMA), hydroxypropyl methacrylate (HPMA), hydroxypropylmethacrylamide, PEG acrylate (PEGA), PEG methacrylate, methacrylate polymers containing 2-methacryloyloxyethyl-phosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly (tetramethylene glycol), hydroxy functional poly(vinyl pyrrolidone), biomolecules such as collagen, chitosan, alginate, fibrin, fibrinogen, cellulose, starch, dextran, dextrin, hyaluronic acid, fragments and derivatives of hyaluronic acid, heparin, fragments and derivatives of heparin, glycosamino glycan (GAG), GAG derivatives, polysaccharide, elastin, elastin protein mimetics, or combinations thereof. Some examples of elastin protein mimetics include (LG-GVG)$_n$, (VPGVG)$_n$, Val-Pro-Gly-Val-Gly, or synthetic biomimetic poly(L-glytanmate)-b-poly(2-acryloyloxyethyllactoside)-b-poly(l-glutamate) triblock copolymer.

In some embodiments of the current invention the polymer used with the device and in the method of this invention can be poly(ethylene-co-vinyl alcohol), poly(methoxyethyl methacrylate), poly(dihydroxylpropyl methacrylate), polymethacrylamide, aliphatic polyurethane, aromatic polyurethane, nitrocellulose, poly(ester amide benzyl), co-poly-{[N,N'-sebacoyl-bis-(L-leucine)-1,6-hexylene diester]$_{0.75}$-[N,N'-sebacoyl-L-lysine benzyl ester]$_{0.25}$}(PEA-Bz), co-poly-{[N,N'-sebacoyl-bis-(L-leucine)-1,6-hexylene diester]$_{0.75}$-[N,N'-sebacoyl-L-lysine-4-amino-TEMPO amide]$_{0.25}$} (PEA-TEMPO), aliphatic polyester, aromatic polyester, fluorinated polymers such as poly(vinylidene fluoride-co-hexafluoropropylene), poly(vinylidene fluoride) (PVDF), poly(vinylidene fluoride-co-hexafluoropropylene-co-tetrafluoroethylene), and Teflon™ (polytetrafluoroethylene), a biopolymer such as elastin mimetic protein polymer, star or hyper-branched SIBS (styrene-block-isobutylene-block-styrene), or combinations thereof. In some embodiments, where the polymer is a copolymer, it can be a block copolymer that can be, e.g., di-, tri-, tetra-, or oligo block copolymers or a random copolymer. In some embodiments, the polymer can also be branched polymers such as star polymers.

Presently preferred polymers for use with this invention include polyesters such as, without limitation, poly(L-lactide), poly(D-lactide), poly(D,L-lactide), poly(meso-lactide), poly(L-lactide-co-glycolide), poly(D-lactide-co-glycolide), poly(D,L-lactide-co-glycolide), poly(meso-lactide-co-glycolide), poly(caprolactone), poly(hydroxyvalerate), poly(hydroxybutyrate), poly(ethylene glycol-co-butylene terephthalate).

Other presently preferred polymers of this invention are fluoropolymers such as poly(vinylidene fluoride-co-hexafluoropropylene). When used, the poly(vinylidene fluoride-co-hexafluoropropylene) preferable at present has a constitutional unit weight-to-weight (wt/wt) ratio of about 85:15. "Constitutional unit" refers to the composition of a monomer as it appears in a polymer. For example, without limitation, the constitutional unit of the monomer acrylic acid, $CH_2=CHC(O)OH$, is —$CH_2$—$CH(C(O)OH)$— The average molecular weight of the presently preferred poly (vinylidene fluoride-co-hexafluoropropylene) polymer is from about 50,000 to about 500,000 Daltons. Further, it is presently preferred that the poly(vinylidene fluoride-co-hexafluoropropylene) polymer used to form a drug reservoir layer herein be semicrystalline. The presently preferred coating thickness of the poly(vinylidene fluoride-co-hexafluoropropylene) drug reservoir layer is from about 1 um to about 20 um.

Blends and copolymers of the above polymers may also be used and are within the scope of this invention. Based on the disclosures herein, those skilled in the art will recognize those implantable medical devices and those materials from which they may be fabricated that will be useful with the coatings of this invention.

As used herein, a "primer layer" refers to a coating consisting of a polymer or blend of polymers that exhibit good adhesion characteristics with regard to the material of which the device body is manufactured and good adhesion characteristic with regard to whatever material is to be coated on the device body. Thus, a primer layer serves as an intermediary layer between a device body and materials to be affixed to the device body and is, therefore, applied directly to the device body. Examples without limitation, of primers include acrylate and methacrylate polymers with poly(n-butyl methacrylate) being a presently preferred primer. Some additional examples of primers include, but are not limited to, poly(ethylene-co-vinyl alcohol), poly (vinyl acetate-co-vinyl alcohol), poly(methacrylates), poly (acrylates), polyethyleneamine, polyallylamine, chitosan, poly(ethylene-co-vinyl acetate), and parylene-C.

As used herein, "drug reservoir layer" refers either to a layer of therapeutic agent applied neat or a therapeutic agent that has been dissolved or dispersed in a polymer matrix. A polymeric drug reservoir matrix is designed such that, by one mechanism or another, e.g., without limitation, by elution or as the result of biodegradation of the polymer, the therapeutic substance is released from the layer into the surrounding environment. A drug reservoir layer may also act as a release rate-controlling layer.

In addition to an optional primer layer and a drug reservoir layer, an implantable medical device of this invention may comprise a topcoat layer. As used herein, a "topcoat layer" refers to a polymeric layer that is disposed over an implantable medical device of this invention such that it comprises the outermost layer of polymer on the device, that is, it is the layer that is in direct contact with the environment in which the device is implanted. A topcoat layer may be biodegradable, which biodegradation may occur relatively slowly if the layer is also serves as a rate controlling layer for the release of the macrocyclic triene lactone drug from the device, or biodegradation may occur rapidly if the topcoat layer serves only as a protective layer for the layers beneath. A topcoat layer may also serve as a compatibility-inducing layer that renders the device more inert with regard to reaction with foreign body-eliminating mechanisms within the body.

As use herein, "disposing" a layer or material onto a particular substrate be it a device body or another layer, refers to a coating of the material applied directly to the exposed surface of the indicated substrate. By "exposed surface" is meant any surface regardless of its physical location with respect to the configuration of the device that, in use, would be in contact with bodily tissues or fluids. "Disposing" may, however, also refer to the application of the layer onto an intervening layer that has been applied to a stent body, wherein the layer is applied in such a manner that, were the intervening layer not present, the layer would be applied to the exposed surface of the indicated substrate. An example of an intervening layer is a primer layer.

Drug eluting stents are also known in which neat drug is applied to all or a portion of the surface of a stent without a matrix polymer in the coating composition. In some cases the surface of the stent to which the neat drug is to be applied is roughened or has features such as pits, depots or grooves to help retain the neat drug on the stent. Another embodiment of a DES that can benefit from the invention herein is a hollow or stent in which the hollow space is at least partially filled with the drug, which then elutes out of the stent through pores created in the surface of the stent.

As used herein, the terms "drug," "therapeutic agent," "active agent" and the like are interchangeable and refer to substances that have been approved by the Food and Drug Administration (FDA), overseas regulatory agencies, notified bodies, or the USDA for use in treatment of diseases and disorders in any animal species, but in particular human beings. In general, a drug, a therapeutic agent or an active agent refers to any substance that, when administered in a therapeutically effective amount to a patient suffering from a disease, has a therapeutic beneficial effect on the health and well-being of the patient. A therapeutic beneficial effect on the health and well-being of a patient includes, but it not limited to: (1) curing the disease; (2) slowing the progress of the disease; (3) causing the disease to retrogress; or, (4) alleviating one or more symptoms of the disease. As used herein, a therapeutic agent also includes any substance that when administered to a patient, known or suspected of being particularly susceptible to a disease, in a prophylactically effective amount, has a prophylactic beneficial effect on the health and well-being of the patient. A prophylactic beneficial effect on the health and well-being of a patient includes, but is not limited to: (1) preventing or delaying on-set of the disease in the first place; (2) maintaining a disease at a retrogressed level once such level has been achieved by a therapeutically effective amount of a substance, which may be the same as or different from the substance used in a prophylactically effective amount; or, (3) preventing or delaying recurrence of the disease after a course of treatment with a therapeutically effective amount of a substance, which may be the same as or different from the substance used in a prophylactically effective amount, has concluded.

A "therapeutically effective amount" refers to that amount of a therapeutic agent that will have a beneficial effect, which may be curative or palliative, on the health and well-being of the patient with regard to the disease or disorder with which the patient is known or suspected to be afflicted. A therapeutically effective amount may be administered as a single bolus, as intermittent bolus charges, as short, medium or long term sustained release formulations or as any combination of these. As used herein, short-term sustained release refers to the administration of a therapeutically effective amount of a therapeutic agent over a period from about several hours to about 3 days. Medium-term sustained release refers to administration of a therapeutically effective amount of a therapeutic agent over a period from about 3 day to about 14 days and long-term refers to the delivery of a therapeutically effective amount over any period in excess of about 14 days. Any reference a therapeutic agent relating to its presence on an implantable medical device or its use in a method of this invention is to be understood as referring to a therapeutically effective amount of that therapeutic agent.

As used herein, "pharmaceutically acceptable" refers to a substance that has been approved by the appropriate agency (ies) for use in animal species, again, in particular, human beings. This includes, of course, drugs but also includes other materials that, while not drugs per se, have a utility in animal species for other purposes. This includes substances that been tested for safety and found to be "generally regarded as safe" (GRAS) in animal species.

As used herein a "pharmaceutically acceptable antioxidant stabilizer" refers to a chemical substance that does not, at least in sufficiently low doses, detrimentally affect the physiological well-being of a patient to whom it has been administered and that is capable of preventing damage to therapeutic agents due to reaction of the agent with oxygen or free radicals released by reaction of oxygen with other entities. For the purpose of this invention, a pharmaceutically acceptable antioxidant includes, without limitation, a butylated phenol, butylated hydroxytoluene (BHT), butylated hydroxyanisole (BHA), t-butylhydroquinone, quinone, an alkyl gallate, methyl gallate, ethyl gallate, propyl gallate, octyl gallate, docecyl gallate, resveratrol, cysteine, n-acetylcysteine, bucillamine, glutathione, 7-hydroxyethylrutoside, carvedilol, vitamin C, ascorbyl palmitate, fumaric acid, a tocopherol, α-tocopherol, α-tocopherol acetate, a tocotrienol, vitamin E, lycopene, a flavonoid, a carotenoid and carotene.

A presently preferred pharmaceutically acceptable antioxidant stabilizer for use in device and methods herein is butylated hydroxytoluene (BHT).

As noted previously, antioxidants of the type used for the stabilization of drugs herein are not particularly beneficial to patients. Significantly, this is not a great problem in theory. Once an implantable medical device has been fabricated and placed in protective packaging or once it has been implanted in a patient's body there appears to be no further need of an antioxidant stabilizer. For example, a Xience Prime stent (Abbott Cardiovascular Systems, Inc.) in which the drug reservoir layer comprises everolimus as the macrocyclic triene lactone drug and BHT as the antioxidant stabilizer and which is packaged in a light-tight package under an Argon atmosphere, shelf life studies have shown that BHT is not necessary for product stability under long term (25° C., 60% relative humidity) or intermediate (30° C., 65% relative humidity) storage conditions. Critical attributes of the coated device such as Total Content, Drug Release and Degradation Product have been found to be unaffected by the absence of BHT on the device. The preceding suggests that it would be beneficial to patients and not detrimental to the modified rapamycin drug to minimize the amount of antioxidant stabilizer on a finished, that is, fully fabricated, implantable medical device.

Thus, in co-pending patent application Ser. No. 13/788,584, which application is filed on even date herewith and which is incorporated by reference as if fully set forth herein, it is taught that a pharmaceutically acceptable antioxidant stabilizer may be included as a component of in one or more layers coated on an implantable medical device in an amount by weight that totals about 0.0001% to about 0.01% of the total amount by weight of macrocyclic triene lactone (which includes the rapamycin derivatives of this invention) present on the device. The Ser. No. 13/788,584 application further teaches that, when the pharmaceutically acceptable antioxidant stabilizer is BHT, a presently preferred antioxidant stabilizer, the rapamycin derivative is everolimus and the implantable medical device is a stent, to arrive at a finished catheter/stent product that has the desired amount of residual BHT, i.e., about 0.0001% to about 0.01% w/w based on the weight of everolimus on the stent, the amount of BHT in the initial coating composition should be about 0.166% w/w BHT or less based on everolimus. Currently, however, everolimus is supplied commercially with 0.2% BHT (w/w), which amount is intended primarily to protect pure everolimus as an isolated solid prior to its incorporation into a coating composition. The present invention removes this requirement since pure everolimus is never isolated as a dry solid permitting the initial amount of BHT to be substantially reduced at all stages of fabrication of a DES comprising everolimus, which it is expected should result in a finished product, e.g., a sterilized stent mounted on a catheter delivery vehicle, with a residual BHT content that is in the range set forth in the Ser. No. 13/788,584 patent application or even lower, even to the point of being non-detectable. A further benefit of the procedure from synthesis to coating and final packaging is that the rapamycin derivative is not isolated as a dry solid and is generally not exposed to any manner of harsh treatment that could result in loss of purity or loss of biological activity.

Figure 2:
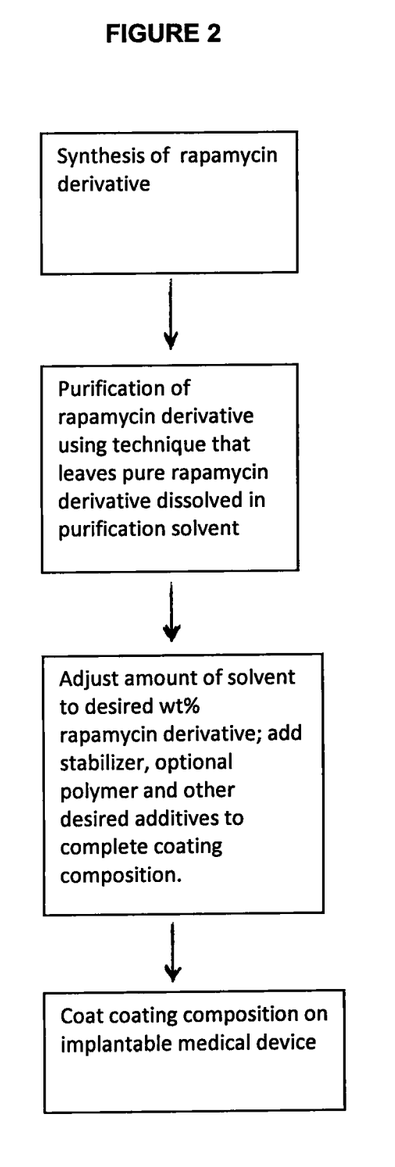
FIG. 2 is a flow chart showing the process of this invention for bringing a rapamycin derivative from synthesis to disposition on a DES and final packaging in a light-tight container under an inert atmosphere.

There is a viable alternative to the primary method of this invention, a method that more closely resembles the current procedure but still avoids the isolation of dry rapamycin derivative and therefore is still novel over the prior art. In this procedure, the rapamycin derivative is recrystallized from an appropriate solvent, in the case of everolimus, ethanol. The still solvent-wetted pure rapamycin derivative is then washed with a small amount of cold recrystallization solvent to remove any vestige of impurities. The recrystallization-solvent-wetted pure rapamycin derivative is then immediately dissolved in an appropriate coating composition solvent and an antioxidant added, again in the case of everolimus, BHT. The remainder of this alternative mirrors the procedure of this invention, as shown in FIG. 2, from this point on.

As used herein, a rapamycin derivative refers to rapamycin that has undergone chemical modification at one or more positions on the molecule. Preparing such a rapamycin derivative is conventionally referred to as "synthesizing" the compound. At present, one preferred position of the modification is the 40-O— position, as such is known and understood by those skilled in the art. Currently preferred 40-O-rapamycin derivatives include everolimus, temsirolimus, deforolimus (ridaforolimus), merilimus and biolimus (umirolimus), although it is understood that other modified, including other 40-O-substituted, rapamycins may be used with the method of this invention and are within the scope hereof. Another preferred position of derivitization of rapamycin is the 16-O-position which includes the rapamycin derivative novolimus. Another useful rapamycin derivative is zotarolimus (AB-578). Lastly, there are useful therapeutic agents with biological activity similar to rapamycin, examples of which include myolimus and 16-pent-2-ynyloxy-32(S)-dihydrorapamycin.

An important part of the rapamycin derivative synthesis process is purification of the final product. This is necessary because of the stringent requirements imposed by regulatory agencies with regard to knowing specifically what and exactly how much of a particular drug is being administered to a patient. Thus, any synthesis of a rapamycin derivative will include one or more purification steps. It is an aspect of this invention that whatever purification method is selected for use in the rapamycin derivative synthesis, it should not require or result in the isolation of the rapamycin derivative as a dry solid. Since purification methods such as, without limitation, elution (column) chromatography, high performance liquid chromatography, high performance countercurrent chromatography, planar chromatography, supercritical fluid chromatography, liquid-liquid extraction, liquid-solid extraction and the like, all of which are within the scope of this invention, result in the purified compound being dissolved in a solvent.

The selected solvent for the purification should, in addition to being suitable for the purification procedure itself, be suitable as a solvent for use in coating a drug reservoir layer on an implantable medical device such as, without limitation, a DES.

A "coating composition" is simply a formulation comprising the selected solvent, the rapamycin derivative, the antioxidant stabilizer and any other additives, excipients or adjuvants that might be desirable in a drug reservoir layer, each of which may be dissolved in or suspended in the selected solvent. In particular, a polymer that will serve as a matrix for the rapamycin derivative drug may be included in the coating composition.

As used herein, a "matrix polymer" refers to a polymer that has been included in the coating composition and that serves as the carrier for the components of the coating composition once the selected solvent has been removed. The matrix polymer is selected in particular so as to have desired drug release properties.

With regard to the selected solvent, to be "suitable" for a purification process referred to herein means in general that the rapamycin derivative should initially be soluble in the chosen solvent. To be suitable as a solvent for the coating composition, the solvent should have an appropriate volatility so that it can be readily removed from the drug reservoir layer once deposited on a device or, if not particularly volatile, such as, without limitation, DMSO, be pharmaceutically acceptable in its own right so that residual solvent in the drug reservoir layer is of no pharmacological significance. With regard to this last possibility especially, it is presently preferred that a solvent selected for the purification/coating composition also meet ICH Tripartite Guidelines for safety. Solvents that exhibit the above characteristics and therefor may be suitable for use in the present method include, without limitation, methanol, ethanol, propanol, n-propanol, isopropanol, butanol, pentane, hexane, heptane, octane, nonane, methyl acetate, ethyl acetate, propyl acetate, butyl acetate, toluene, xylene, acetone, methyl ethyl ketone (MEK), cyclopentanone, cyclohexanone, diethyl ether, dipropyl ether, diisopropylether, tetrahydrofuran, dioxane, dimethyl formamide, dimethylacetamide and dimethyl sulfoxide.

In the coated drug reservoir layer, the rapamycin derivative of this invention may be essentially crystalline, essentially amorphous or anywhere in between. By "essentially crystalline" or "essentially amorphous" is meant that, while the bulk of a sample of the rapamycin derivative will exhibit the characteristics of crystallinity or amorphousness, a small amount of the other particle form may still be detected in the sample. It is presently preferred that the rapamycin derivative be at least essentially amorphous, more preferably completely amorphous within the detection limit of an appropriate method to detect crystalline drug in a coating as, for example without limitation, by differential scanning calorimetry.

As mentioned previously, rapamycin derivatives are oxygen sensitive due to the presence of the conjugated triene, i.e., three double bonds linked together by a single bond between the first and the second and a single bond between the second and the third. Since it is desirable, if not essential, that the composition and quantity of an active agent being administered to a patient, regardless of the manner of administration, be accurately known, it is highly desirable to control as well as possible any mechanism that might detrimentally affect the active agent before it is administered. Oxidation of compounds often has such a detrimental effect on active agents and is to be controlled. With regard to delivery of macrocyclic triene lactone active agents of this invention using implantable medical devices such as stents, a solution to this problem lies in the inclusion of pharmaceutically acceptable antioxidant compounds in the drug reservoir layer during the fabrication of the device. As noted previously "pharmaceutically acceptable" as used herein means that the antioxidants that are useful in this invention have been found acceptable for use in humans by the Food and Drug Administration (FDA, in the United States; equivalent foreign governmental agencies would be charged with such approvals in their respective countries). Of course, antioxidants that may in the future be found acceptable for human use by the FDA are clearly within the scope of this invention. Antioxidants curtail oxidation of macrocyclic triene lactones by several well-known mechanisms such as radical scavenging and complexation with pro-oxidation metal species. BHT, a presently preferred antioxidant for use with an implantable medical device of this invention, is of the former type, i.e., it functions as a free radical scavenger.

If desired it is entirely possible, and in fact is an aspect of this invention, to include another therapeutic agent or agents along with the rapamycin derivative on an implantable medical device hereof. If the other agent(s) are known to not be oxygen sensitive, then no changes need be made to the disclosure herein of the amount of antioxidant to use. If, on the other hand, any of the additional therapeutic agents are known to be oxygen sensitive, then the total amount of antioxidant used may be determined as set forth above except that the total amount of macrocyclic triene lactone plus the amount of any other oxygen sensitive therapeutic agent(s) is used in the experiments performed to determine the effect of the fabrication steps on the amount of antioxidant stabilizer consumed during each phase of the fabrication.

Among other therapeutic agents that may be suitable for use in this invention, anti-inflammatory compounds are particularly presently preferred. Suitable anti-inflammatory agents that can be used in combination with the macrocyclic triene lactpmes herein include, without limitation, dexamethasone, dexamethasone acetate, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus and prodrugs, co-drugs and combinations thereof.

Other therapeutic agents that may be suitable for use in the methods herein include anti-neoplastic, antimitotic, antiplatelet, antifebrin, antithrombin, cytostatic and anti-proliferative agents.

Antineoplastic or anti-mitotic agents include, without limitation, paclitaxel, docetaxel, protaxel, methotrexate, azathioprine, vincristine, vinblastine, fluorouracil, doxorubicin hydrochloride, and mitomycin.

Antiplatelet, anticoagulant, antifibrin, and antithrombin agents include, without limitation, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as Angiomax ä, calcium channel blockers such as nifedipine, colchicine, fish oil (omega 3-fatty acid), histamine antagonists, lovastatin, monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO) and estradiol.

Cytostatic or anti-proliferative agents include, without limitation, angiopeptin, angiotensin converting enzyme inhibitors such as captopril, cilazapril or lisinopril, calcium channel blockers such as nifedipine; colchicine, fibroblast growth factor (FGF) antagonists; fish oil ($\omega$-3-fatty acid); histamine antagonists; lovastatin, monoclonal antibodies such as, without limitation, those specific for Platelet-Derived Growth Factor (PDGF) receptors; nitroprusside, phosphodiesterase inhibitors, prostaglandin inhibitors, suramin, serotonin blockers, steroids, thioprotease inhibitors, triazolopyrimidine (a PDGF antagonist) and nitric oxide.

Other potentially useful therapeutic agents include, without limitation, alpha-interferon, genetically engineered epithelial cells, DNA and RNA nucleic acid sequences, antisense molecules, and ribozymes, antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides, retroviral vectors; antiviral agents; analgesics; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers, beta-blockers such as pindolol, antiarrhythmics; antihypertensives; diuretics; vasodilators including general coronary; peripheral and cerebral; central nervous system stimulants; cough and cold preparations, including decongestants; hypnotics; immunosuppressives; muscle relaxants; parasympatholytics; psychostimulants; sedatives; tranquilizers; natural or genetically engineered lipoproteins; and restenosis reducing agents.

Thus, the method of this invention may comprise the following steps: A desired rapamycin derivative is synthesized using synthetic chemical reactions and procedure either currently well-known to those skilled in the art or as may be uniquely arrived at to accomplish the desired synthesis. The rapamycin derivative is then purified using a method that permits the use of a solvent that has been determined to be suitable for use in the purification per se, in the preparation of a coating composition and in the application of the coating composition to an implantable medical device as discussed above. Such method may comprise, without limitation, elution (column) chromatography, high performance liquid chromatography, high performance countercurrent chromatography, planar chromatography, supercritical fluid chromatography, liquid-liquid extraction and liquid-solid extraction. The purified rapamycin derivative is left in the solvent used for the purification. The amount of purified rapamycin derivative desired in the coating composition, usually as a weight percent rapamycin derivative in the coating solvent is selected. The actual weight percent rapamycin derivative in the purification solvent is determined and, if the percentages are not the same, purification solvent is added to or removed from the mixture containing the rapamycin derivative. If solvent needs to be removed, it is preferable to do so under the mildest conditions possible. Distillation of the solvent under reduced pressure, i.e., vacuum distillation, is a preferred method of removing solvent. The process may require heating but the temperature should be carefully selected so as to not cause any degradation of the rapamycin derivative. The effect of temperature on any particular rapamycin can, of course, be predetermined empirically.

Once the percent rapamycin in the purification solvent is adjusted, an antioxidant stabilizer is added to the mixture as a weight percent based on the amount of rapamycin derivative present. The result is a coating composition ready for disposition on an implantable medical device. It is possible, however, and is an aspect of this invention, that a polymer be added to the coating composition. The polymer will act as a matrix within which the rapamycin derivative, the antioxidant and the other excipients, adjuvants and the like are suspended when solvent(s) is(are) removed. The polymer is selected so as to have desired mechanical, biological, and in the case of a bioresorbable polymer, degradation properties and desired drug release properties for the selected rapamycin derivative. Once again, these properties are either known or readily determined by those skilled in the art and need not be specifically described herein. Any such rapamycin derivative/polymer combination is within the scope of this invention as is the addition of other excipients or other drugs or both.

The dissolved or dispersed rapamycin derivative drug is then applied to an implantable medical device by spray coating to form a drug reservoir layer. Spray coating may comprise a one-pass process or a plurality of passes to achieve the desired coating thickness and quantity of drug on the implantable device.

The spray coated implantable device is then dried at an elevated temperature, which, as above, is selected so as to have no detrimental effect on the rapamycin derivative drug, that is, a temperature that is empirically determined by experimentation to be acceptable.

The implantable medical device comprising at least the drug reservoir layer is then mounted on a delivery vehicle and the mounted device/catheter is sterilized. The delivery vehicle can be any manner of device intended to convey an implantable medical device to and, at the appropriate time, release the implantable medical device at a treatment site in a patient's body. In the case of a DES, the stent is usually mounted on a catheter as the delivery vehicle.

Sterilization of the mounted device can be accomplished by ethylene oxide sterilization, e-beam sterilization or gamma sterilization, all of which are well-known to those skilled in the art and require no detailed description herein.

The sterilized device/carrier vehicle is then ready for use or for storage as discussed above, i.e., in a light-tight package under an inert gas atmosphere.

Figure 1:
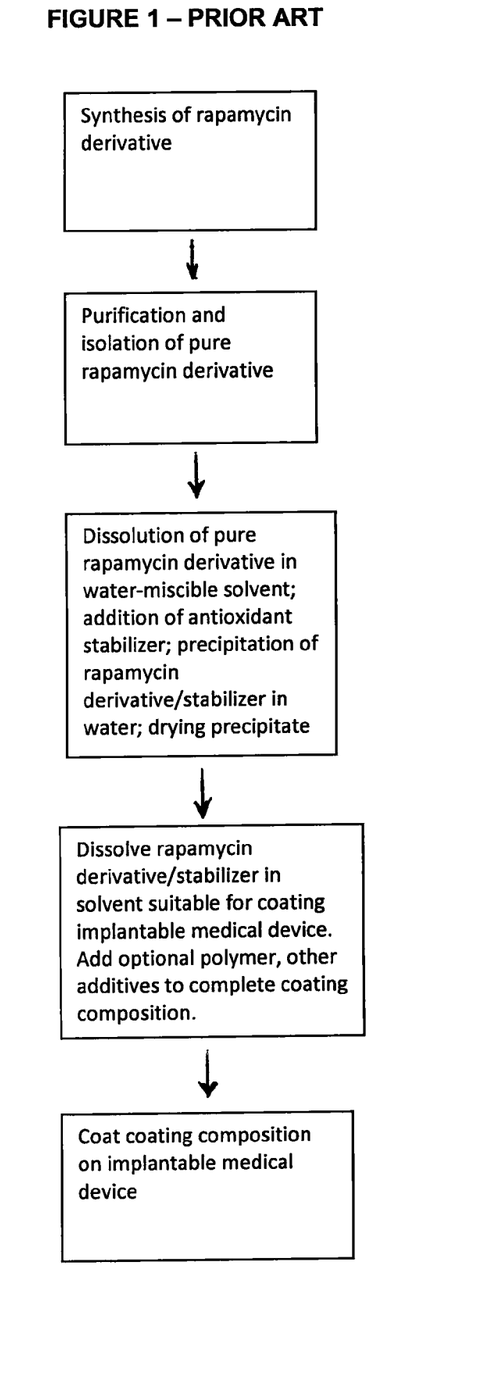
FIG. 1 is a flow chart showing a prior art process for bringing a rapamycin derivative from synthesis to disposition on a DES and final packaging in a light-tight container under an inert atmosphere.

The novelty of the present invention can readily be seen by comparing FIG. 1, the current process from synthesis of the rapamycin derivative to the coating of a drug reservoir layer comprising the rapamycin derivative on an implantable medical device. For purposes of clarity and concreteness, the following description is directed specifically to everolimus as the rapamycin derivative, BHT as the pharmaceutically acceptable antioxidant stabilizer and a vascular stent as the implantable medical device. It is to be understood, however, that the same or obviously similar steps are expected to pertain to virtually any rapamycin derivative. Thus, FIG. 1, Step 1 is directed to the actual synthesis of everolimus. Step 2 is the purification of the everolimus by recrystallization from an appropriate solvent system. For everolimus, the current preferred solvent system is a mixture of an ester, such as, without limitation, ethyl acetate, and a hydrocarbon such as, without limitation, heptane. This process results in pure crystalline everolimus. The pure crystalline everolimus is then dissolved in another solvent, presently an alcohol such as, without limitation, ethanol, and a desired amount of BHT is added to the solution (FIG. 1, Step 3). The amount of BHT is presently preferred to be in the range of 0.01 to 0.5 percent by weight based on the amount of everolimus in the solution; most preferably, and the amount of BHT combined with everolimus as currently commercially provided is about 0.2%. The alcohol solution is then carefully added to a large volume of water over an extended period of time resulting in the precipitate of everolimus/0.2% BHT from the ethanol/water as an amorphous solid (FIG. 1, Step 3). The amorphous solid is dried, packaged under inert atmosphere, and shipped to, for example, a manufacturer of medical devices. In FIG. 1, Step 4, the everolimus/BHT is re-dissolved in a solvent suitable for preparation of a coating composition and for coating on a stent as a drug reservoir layer. At this point it is possible to introduce a polymer to the coating composition to act as a matrix for the suspension of all the components of the coating composition once the solvent is removed. Finally, in FIG. 1, Step 5, the coating composition is applied to the stent to form a drug reservoir layer. This final step may include other sub-steps such as the application of a topcoat layer, etc. but these steps, for the purposes of this example may be considered to be identical for both FIG. 1 and FIG. 2, are well-known to those skilled in the art and need not be discussed at length here.

In stark contrast to the above, FIG. 2, the novel process of this invention, consists essentially of the following steps:

FIG. 2, Step 1, is the same as FIG. 1, Step 1: synthesis of everolimus. In FIG. 1, Step 2, however, the processes diverge. Whereas FIG. 1, Step. 2 was a recrystallization step, which by it nature requires isolation of the crystallized everolimus from impurities remaining in the recrystallization solvent, FIG. 2, Step 2 involves a purification procedure that results in pure everolimus dissolved in the purification solvent. Such purification techniques include, without limitation, elution (column) chromatography, high performance liquid chromatography, high performance countercurrent chromatography, planar chromatography, supercritical fluid chromatography, liquid-liquid extraction and liquid-solid extraction. The critical factor is that the selected technique results in pure everolimus dissolved in solvent. As mentioned previously, the solvent should be one that is suitable for use in a coating composition and actual application of a coating to a stent. In any event, in FIG. 2, Step 3, the amount of everolimus as a weight percent of the total everolimus/solvent solution is determined and a selected amount of BHT is added. If desired a selected amount of a matrix polymer may also be added at this step. The percent everolimus desired in the coating composition is then achieved by adding to or removing solvent from the everolimus/BHT/optional polymer solution. Of course, other solvents, excipients, additives, active agents, etc. in calculated amounts may also be added at this step. In any event, the result of FIG. 2, Step 2, is a coating composition ready for application to a stent. In FIG. 2, Step 3, the coating composition is applied to the step and then, as with in FIG. 1, additional steps are carried out such as drying the applied coating to form drug reservoir layer, mounting the stent on a catheter, sterilizing the entire assembly and finally packaging the assembly in a light-tight, container under an inert atmosphere, wherein, as discussed above, the everolimus has been shown to be sufficiently stable for storage.

As is readily apparent, the inventive process of FIG. 2 requires fewer separate steps, less manipulation of rapamycin derivative drugs, especially in the dry state, and is substantially more gentle on the everolimus that the current process as set forth in FIG. 1.

What is claimed:

1. A method of fabricating an implantable medical device comprising a rapamycin derivative drug, the method comprising:
    synthesizing a rapamycin derivative drug;
    purifying the rapamycin derivative drug using a technique that results in a substantially pure rapamycin derivative drug dissolved in a solvent, wherein:
        the solvent used in the purification technique is used for preparation of a coating composition comprising the rapamycin derivative drug;
    determining the percent by weight of the rapamycin derivative drug in the solvent;
    adjusting the amount of the solvent such that the weight percent of the rapamycin derivative drug in the solvent is that desired in the coating composition to be applied to an implantable medical device;
    adding a desired weight percent, based on the weight of the rapamycin derivative drug, of an pharmaceutically acceptable antioxidant stabilizer to form the coating composition; and
    disposing the coating composition on the implantable medical device to form a drug reservoir layer;
    wherein the substantially pure rapamycin derivative drug is not isolated as a dry solid after the purifying step and before the disposing step.

2. The method of claim 1, further comprising addition of a matrix polymer to the coating composition before disposing the composition on the implantable medical device.

3. The method of claim 1, further comprising drying the drug reservoir layer.

4. The method of claim 2, further comprising mounting the implantable medical device on a carrier vehicle.

5. The method of claim 4, wherein the carrier vehicle is a catheter.

6. The method of claim 5, wherein the carrier vehicle with mounted implantable device is sterilized.

7. The method of claim 6, wherein sterilization comprises ethylene oxide sterilization, e-beam sterilization or gamma sterilization.

8. The method of claim 7, wherein the sterilized carrier vehicle with mounted implantable device is packaged in a light-tight container under an inert atmosphere.

9. The method of claim 1, wherein the synthesized rapamycin derivative drug is selected from the group consisting of a 40-O-substituted rapamycin, everolimus, temsirolimus, deforolimus, ridaforolimus, merilimus, biolimus, umirolimus and 16-pent-2-ynyloxy-32 (S)-dihydrorapamycin.

10. The method of claim 1, wherein the synthesized rapamycin derivative drug is selected from the group consisting of zotarolimus, 16-pent-2-ynyloxy-32 (S)-dihydrorapamycin, novolimus, and myolimus.

11. The method of claim 1, wherein the pharmaceutically acceptable antioxidant stabilizer is selected from the group consisting of a butylated phenol, butylated hydroxytoluene (BHT), butylated hydroxyanisole, t-butylhydroquinone, quinone, an alkyl gallate, methyl gallate, ethyl gallate, propyl gallate, octyl gallate, docecyl gallate, resveratrol, cysteine, n-acetylcysteine, bucillamine, glutathione, 7-hydroxyethylrutoside, carvedilol, vitamin C, ascorbyl palmitate, fumaric acid, a tocopherol, α-tocopherol, α-tocopherol acetate, a tocotrienol, vitamin E, lycopene, a flavonoid, a carotenoid, carotene and combinations thereof.

12. The method of claim 11, wherein the pharmaceutically acceptable antioxidant stabilizer is BHT.

13. The method of claim 1, wherein purifying the synthesized rapamycin derivative drug is selected from the group consisting of elution (column) chromatography, high performance liquid chromatography, high performance countercurrent chromatography, planar chromatography, supercritical fluid chromatography, liquid-liquid extraction and liquid-solid extraction.

14. The method of claim 13, wherein the solvent used in the purification process that is also suitable as a solvent for the coating composition is selected from the group consisting of methanol, ethanol, propanol, n-propanol, isopropanol, butanol, pentane, hexane, heptane, octane, nonane, methyl acetate, ethyl acetate, propyl acetate, butyl acetate, toluene, xylene, acetone, methyl ethyl ketone (MEK), cyclopentanone, cyclohexanone, diethyl ether, dipropyl ether, diisopropyl ether, tetrahydrofuran, dioxane, dimethyl formamide, dimethylacetamide, dimethyl sulfoxide and combinations thereof.

15. The method of claim 1, wherein adjusting the amount of solvent to give the desired percent by weight of the rapamycin derivative drug in the solvent comprises removing solvent from or adding solvent to the coating composition.

16. The method of claim 2, wherein the matrix polymer is selected from the group consisting of a polyester, poly(L-lactide), poly(D-lactide), poly(D,L-lactide), poly(meso-lactide), poly(L-lactide-co-glycolide), poly(D-lactide-co-glycolide), poly(D,L-lactide-co-glycolide), poly(meso-lactide-co-glycolide), poly(caprolactone), poly(L-lactide-co-caprolactone), poly(glycolide-co-caprolactone), poly(hydroxyvalerate), poly(hydroxybutyrate), poly(ethylene glycol-co-butylene terephthalate), poly(n-butyl methacrylate), a fluoropolymer, poly(vinylidene fluoride-co-hexafluoropropylene) and blends and copolymer thereof.

17. The method of claim 16, wherein the matrix polymer is poly(vinylidene fluoride-co-hexafluoropropylene).

18. The method of claim 1, wherein disposing the coating composition on the implantable medical device to form the drug reservoir layer comprises spray coating.

19. The method of claim 1, wherein the implantable medical device is a stent.

20. The method of claim 2, wherein the implantable medical device is a stent.

21. The method of claim 20, wherein the pharmaceutically acceptable antioxidant stabilizer is BHT.

22. The method of claim 21, wherein the rapamycin derivative drug is everolimus or novolimus.

23. The method of claim 22, wherein when the rapamycin derivative drug is everolimus, the weight percent BHT based on the weight of everolimus present on the stent is about 0.001 to about 0.01%; and wherein when the rapamycin derivative drug is novolimus, the weight percent BHT based on the weight of novolimus present on the stent is about 0.001 to about 0.01%.

24. The method of claim 22, wherein the amount of BHT remaining on the stent after all of the process steps are completed is non-detectable.

* * * * *